United States Patent [19]

Larimore et al.

[11] 4,352,359
[45] Oct. 5, 1982

[54] BIOMEDICAL ELECTRODE

[75] Inventors: Franklin C. Larimore, Shoreview; Steven M. Heilmann, North St. Paul, both of Minn.

[73] Assignee: Minnesota Mining and Manufacturing Company, St. Paul, Minn.

[21] Appl. No.: 155,191

[22] Filed: Jun. 2, 1980

Related U.S. Application Data

[63] Continuation of Ser. No. 940,734, Sep. 8, 1978, abandoned, which is a continuation-in-part of Ser. No. 825,870, Aug. 19, 1977, abandoned.

[51] Int. Cl.³ .............................................. A61B 5/04
[52] U.S. Cl. .................................... 128/640; 128/802
[58] Field of Search .............. 128/640, 641, 798, 802, 128/803, 303.13

[56] References Cited

U.S. PATENT DOCUMENTS

| | | | |
|---|---|---|---|
| 2,555,037 | 5/1951 | Jensen | 128/803 X |
| 3,911,906 | 10/1975 | Reinhold, Jr. | 128/641 |
| 3,946,730 | 3/1976 | Monter | 128/641 |
| 3,989,050 | 11/1976 | Buchalter | 128/419 R |
| 3,993,049 | 11/1976 | Kater | 128/640 |
| 3,998,215 | 12/1976 | Anderson et al. | 128/641 |
| 4,002,221 | 1/1977 | Buchalter | 128/660 X |
| 4,066,078 | 1/1978 | Berg | 128/641 |
| 4,125,110 | 11/1978 | Hymes | 128/641 |

*Primary Examiner*—Lee S. Cohen
*Attorney, Agent, or Firm*—Cruzan Alexander; Donald M. Sell; Carolyn A. Bates

[57] ABSTRACT

An essentially dry, disposable biomedical electrode is disclosed having an improved electrically-conductive material at the interface between the electrode and the skin. The conductive material comprises a dermally-nonirritating cohesive, conformable, synthetic hydrophilic polymer containing at least 5 mole percent of monomer units containing a salt of a carboxylic acid.

13 Claims, 2 Drawing Figures

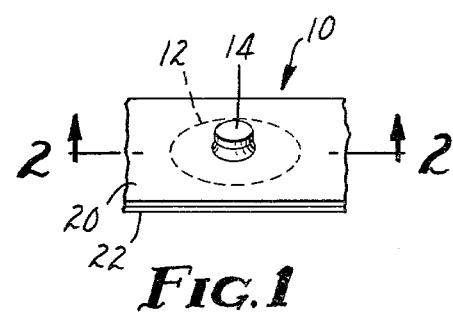
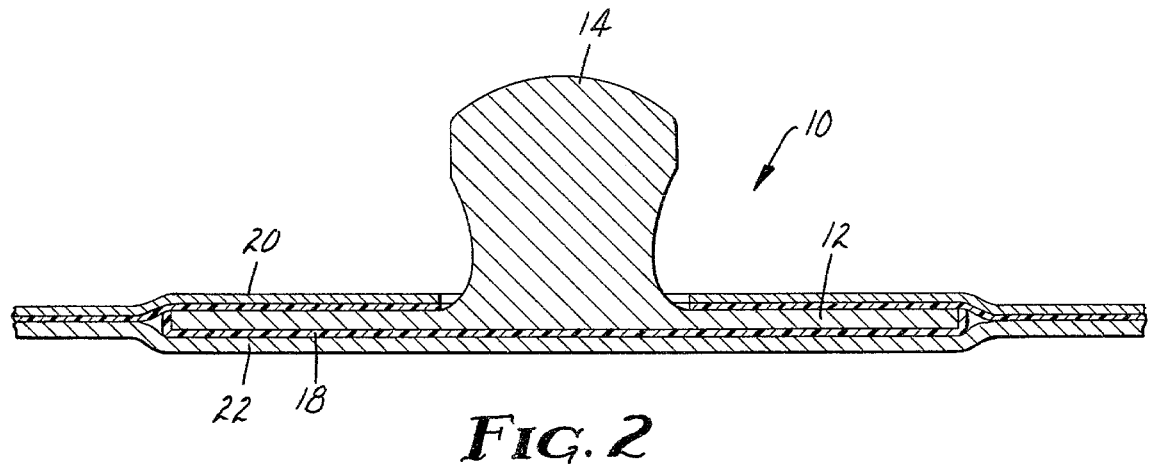

BIOMEDICAL ELECTRODE

This application is a continuation of application Ser. No. 940,734 filed Sept. 8, 1978, now abandoned, which is a continuation-in-part of application Ser. No. 825,870, filed Aug. 19, 1977, now abandoned.

This invention relates to disposable electrodes, often termed "biomedical" electrodes, for establishing an electrical connection between the skin of the human anatomy and an electromedical apparatus, such as a high impedance electromyograph, electrocardiograph, electrostimulator for pain relief, and the like. More particularly it relates to so called "dry" bioelectrodes which do not require the use of messy creams or gels to enhance conductivity between the skin and the electrode plate.

A variety of disposable biomedical electrodes are known in the art. Generally, they comprise a metallic electrode plate adapted for connection to a lead wire which is, in turn, attached to the electromedical apparatus. Typically, a conductive paste, cream, or gel is relied upon for improving the electrical connection and reducing electrical resitance between the skin of the patient and the electrode plate. An adhesive tape is commonly used to adhere the entire apparatus to the skin. Examples of electrodes of this general type are described in U.S. Pat. Nos. 3,587,565 and 3,805,769.

The conductive pastes, creams, or gels used in these prior art biomedical electrodes are unpleasant to use, sloppy, and often irritating to the skin, particularly when the skin is cleaned and abraded prior to application of the electrode. Since these electrodes all contain water as the major ingredient of the conductive material and generally depend on water for suitable electrical performance, they require elaborate packaging to prevent loss of water prior to use. Furthermore, they leave a residue on the skin after removal of the electrode which requires cleanup. A further disadvantage of many electrodes utilizing conductive pastes, creams, or gels is that they develop an overpotential in defibrillation procedures unless the surface of the electrode plate is of expensive silver/silver chloride.

The messy, unpleasant, and inconvenient nature of electrodes using conductive gels or creams has been somewhat alleviated by impregnating a porous pad with the conductive material as shown, for example, in U.S. Pat. Nos. 3,845,757 and 3,901,218. However, elaborate packaging is still required, and, in use, the gel tends to dry out causing variations in the electrical impedance and subsequent signal quality.

To overcome many of the problems associated with so called "wet" electrodes, biomedical electrodes have been proposed which utilize "dry" conductive material. U.S. Pat. Nos. 3,565,059 and 3,911,906 disclose biomedical electrodes utilizing adhesives impregnated with conductive particles. These adhesives serve the dual purpose of enhancing conductivity with the skin and securing the electrode to the skin. Although avoiding the sloppiness and packaging problems associated with gels and pastes, such electrodes generally do not provide satisfactory electrical connection to the skin because the presence of the conductive filler results in a high signal-to-noise ratio and is deleterious to adhesion. Generally, the use of non-homogeneous conductive formulations in bioelectrodes has been found to give rise to noisy electrical signals. It is speculated that dispersed metal or salt particles in a binder matrix form a discontinuous, electrically conductive path which develops random, non-uniform electrical fields between particles which causes noise.

U.S. Pat. No. 3,993,049 discloses a biomedical electrode having a salt dispersed in an adhesive layer. The adhesive layer secures the electrode to the skin, and the salt serves as the current carrier. Preferably, the salt has a cation of the metal that forms the surface of the electrode plate, e.g., silver halide with a silver electrode plate. It is also preferred to include metal powders in the adhesive or provide a metal screen on which the adhesive is carried. The preferred adhesives are water-soluble. This biomedical electrode requires the addition of extraneous material, i.e., a salt solution and metal powders, into the adhesive layer in order to obtain acceptable electrical conductivity. This increases the possibility of skin irritation as well as increases the overall cost of the electrode.

Although the predominance of the art in the field of biomedical electrodes as described above is directed to recording electrodes useful in diagnostics, there is an increasing amount of art appearing that describes grounding electrodes and electrodes for electrical stimulation of parts of the anatomy for purposes of aiding in healing of injuries or trauma or the like. For the most part, the variously described grounding and stimulating bioelectrodes are larger in area than the recording electrodes so that greater current densities can be used without burning body tissue. Generally, these larger electrodes use an electrolyte solution, gel, or paste to provide electrical contact between the body surface and the electrode. Patents describing such electrodes include, for example, U.S. Pat. No. 3,817,252 describing a body conformable electrode utilizing a "diffuser screen" and a conductive paste; No. 3,848,600 describing a contoured electrode utilizing an aqueous salt solution containing 0.2 to 8% neutralized mucilage as electrolyte; and No. 3,964,477 describing an electrode utilizing a porous silver-silver chloride electrode and an electrolyte solution. All of these electrodes utilize an undesirably messy electrolyte.

Another biomedical electrode used for transcutaneous electrical neural stimulation which has been called to the applicants' attention utilizes a natural polymer, namely, gum karaya, for securing the electrode to skin. Gum karaya is a complex polysaccharide combined with certain metallic cations, such as sodium, potassium, calcium, or magnesium. The gum does not dissolve but swells in water to a paste-like gel (Kirk-Othmer, Encyclopedia of Chemical Technology, Vol. 10, 1966). Because natural polymers originate in nature where soil and climatic conditions are variable, and the conditions under which they are collected and processed are variable, there is a great inconsistency in the physical and chemical properties of natural polymers and in the amount of impurities present. Such inconsistency leads to variations in the electrical performance of biomedical electrodes made from natural polymers. This variation in electrical performance cannot be tolerated in biomedical electrodes where consistent electrical properties are important. Furthermore, the natural polymers are undesirable because they generally support undesirable microbial growth and have the potential for creating adverse skin sensitivites including allergenic and antigenic reactions (Merck Index, 8th Edition, 1969, page 598).

"Dry" stimulating electrodes are also known. U.S. Pat. No. 3,812,861 teaches a grounding electrode consisting of a flexible sheet of paperboard coated on both sides with a conductive foil joined electrically together and a means for tightening the device around a limb. Such electrodes having a metal-to-tissue interface are undesirable because of the bio-incompatability of most metals and the difficulty of obtaining adequate conformability with the body surface. U.S. Pat. No. 3,994,302 describes an implantable stimulating electrode wherein the tissue contacting surface is an ion-exchange resin material, such as, for example, quaternized vinyl pyridine grafted to polyethylene. For use, the electrode may be activated by an aqueous solution. This electrode does not appear to be useful on the surface of the skin.

The need to use messy gels, expensive electrode coatings, electrode packaging, and variable natural materials that can be supportive of microbial growth or cause adverse skin reactions has been eliminated by the present invention. It has been discovered that certain homogeneous, synthetic polymers and polymeric formulations can function as effective electrically conductive materials in biomedical electrodes without the necessity of dispersing particulate matter or salts therein.

According to the present invention there is provided an improved, essentially dry, disposable biomedical electrode comprising an electrode plate having on one surface thereof means for electrical connection to an electro-medical apparatus and on the opposite, body contacting surface thereof, an electrically conductive material wherein the electrically conductive material comprises a dermally non-irritating, conformable, cohesive, synthetic, hydrophilic polymer containing at least 5 mole percent of monomer units containing a salt of a carboxylic acid. The biomedical electrode of the invention has an impedance value of 500 Kohms or less at a frequency of 10 Hertz.

The dry bioelectrode of the invention offers several advantages over conventional prior art electrodes. The skin may be prepared with either water or a normal saline solution instead of alcohol which tends to be irritating. There is no need to wait for the skin to dry completely before attaching the electrode because adhesion of the electrode to the skin is enhanced by dampening the skin. The electrode can be made smaller in diameter and thickness than currently available disposable electrodes thus improving comfort and convenience, particularly in long-term monitoring. Application of the electrode is dry, not sloppy or messy as is often the case with electrodes which use creams or gels to enhance conductivity. No costly surface treatment of the electrode plate is required in order to render it suitable for use in connection with defibrillation procedures. No packaging is necessary other than a paper cover to protect the adhesive surface, whereas many currently-available electrodes require elaborate and expensive packaging to prevent crushing and drying of the wet electrolyte materials. Furthermore, when the electrode is removed from the skin of a patient no messy residue remains on the skin.

The term "conformable" is used herein refers generally to the compliance of the conductive material. It must be sufficiently compliant to conform to the surface of the skin beneath the electrode plate to provide a high surface area of contact between the skin and the electrode plate. The important conformability requirement for materials used according to the present invention is generally satisfied by Williams Plasticity values (as described in U.S. Pat. No. 3,725,121) between 0.5 to 4.0 millimeters for thermoplastic formulations. When a copolymer has been crosslinked by one of a variety of known procedures to improve its cohesive properties, the crosslinking may render the formulation insoluble and non-flowing. Such materials cannot be evaluated by the Williams Plasticity measurement which requires flow. A description of glass transition temperature is helpful to distinguish suitably conformable materials of this type. A general account of glass transition temperatures and physical characteristics is found in J. D. Ferry's text entitled "Viscoelastic Properties of Polymers" (Wiley: New York, Chapter 2 (1970)). Generally, crosslinked polymers having a glass transition temperature between −20° to −95° C. are suitably conformable.

The term "hydrophilic carboxylate-containing polymer" as used hereinafter refers to a large molecule built up by the repetition of a sufficient number of small chemical units, of which at least 5 mole percent contain a carboxylic acid group which has been neutralized to form a salt group. To provide cohesive and film-forming properties, generally a polymer having a weight-average molecular weight of at least about 10,000 and preferably 100,000 is required.

The term "synthetic" as used herein refers to those hydrophilic carboxylate-containing polymers which have been synthesized in contrast to those polymers which are collected in nature and simply processed to remove foreign matter such as dirt, leaves, and insects, and on which no chemical reaction has been performed. The term "synthetic" also includes polymers which have been made by chemical modification of a natural polymer to alter its chemical structure and standardize its chemical and physical properties.

The term "cohesive" refers to the internal integrity of the conductive material. Generally, the conductive material is film-forming and must be more cohesive than adhesive to the skin so that, when the electrode is removed from the skin, the conductive layer remains intact and does not leave an objectionable residue.

Hydrophilic carboxylate-containing polymers suitable for use as the electrically conductive material of the biomedical electrode of the invention can be any dermally-nonirritating, cohesive, film-forming, synthetic, polymer selected from the following classes:

A. water-soluble carboxylate-containing polymers;
B. water-soluble carboxylate-containing interpolymers; and
C. hydrophilic water-insoluble interpolymers of water-insoluble monomers and at least 5 mole percent of water-soluble monomers containing carboxylate functionality.

The water-soluble carboxylate-containing polymers of Class A are prepared in accordance with well known methods by homopolymerization or interpolymerization of two or more members of the group of carboxylate salts derived from the acid-base reaction of a Group I metal (of the Periodic Table) hydroxide, carbonate, or bicarbonate, an amine, or a quaternary ammonium hydroxide, carbonate, or bicarbonate and an olefinic, addition-polymerizable carboxylic acid such as acrylic acid, methacrylic acid, maleic acid, fumaric acid, itaconic acid, aconitic acid, and citraconic acid. Alternatively, the olefinic, addition-polymerizable carboxylic acid or acids can be homo- or interpolymerized and subsequently reacted with the above described bases to form the water-soluble carboxylated polymers. The latter method of preparation is preferred in general because higher molecular weight polymers are obtained.

The water-soluble carboxylated interpolymers of Class B are prepared by interpolymerization of the olefinic, addition-polymerizable carboxylic acids described above and olefinic, addition-polymerizable monomers free of carboxylic acid functionality which include, but are not limited to:

- acrylate esters such as methyl acrylate, methyl methacrylate, butyl acrylate, iso-octyl acrylate, dodecyl methacrylate, octadecyl methacrylate, and cyclohexyl acrylate;
- vinyl ethers such as methyl vinyl ether, 2-ethylhexyl vinyl ether, decyl vinyl ether, and octadecyl vinyl ether;
- vinyl acylates such as vinyl acetate, vinyl butyrate, and vinyl dodecanoate;
- olefins such as ethylene, propylene, styrene, α-methylstyrene, 4-chlorostyrene, iso-butylene, and vinyl-cyclohexane;
- olefinic polycarboxylic acid esters such as dimethyl maleate, dimethyl fumarate, and diethyl itaconate; and
- vinyl halides such as vinyl chloride and vinylidene dichloride.

Class B interpolymers are prepared by well known polymerization techniques and are transformed into water-soluble carboxylate-containing interpolymers in a similar fashion as described above with the Class A polymers by a neutralization reaction with a Group I metal hydroxide, carbonate, or bicarbonate, amine, or quaternary ammonium hydroxide, carbonate, or bicarbonate.

The hydrophilic, water-insoluble carboxylate-containing interpolymers of Class C represent a special class of Class B interpolymers differentiated by their solubility in water. They are prepared using the same monomers and procedured as in Class B only the carboxylate-containing monomer is employed at a level less than the amount that will yield a water-soluble interpolymer, e.g. below about 25 mole percent depending on the non-carboxyl-functional, olefinic, addition-polymerizable comonomers employed. The advantage attributable to the Class C materials is that with molar carboxylate levels greater than 5 percent impedance values less than the impedance limit of 500 Kohms (believed to represent a practical upper limit with state of the art electrocardiography and biofeedback electrical instruments) are achieved and pressure sensitive adhesive performance is optimum. Materials that are pressure sensitive adhesives are especially preferred materials of the invention because no additional means of securing the electrode to the skin is necessary.

Pressure sensitive adhesives are well known in the art, and are best described as possessing a four-fold balance of adhesion, cohesion, stretchiness, and elasticity properties as discussed, for example, in U.S. Pat. No. Re. 24,906. This balance of properties is most generally accomplished by the interpolymerization of monomers which if homopolymerized would yield a polymer of relatively high glass transition temperature (ca > 80° C.) or so-called "hard" monomers with monomers which if homopolymerized would yield a polymer of relatively low glass transition temperature (ca < −25° C.) or so-called "soft" monomers. The "hard" monomers employed in the present invention are the carboxyl- or carboxylate-containing, olefinic, addition-polymerizable monomers hereinbefore described, while the "soft" monomers are the non-carboxyl- or non-carboxylate-containing, olefinic, addition-polymerizable monomers that contain relatively large alkyl residues containing about 4 to 12 carbon atoms. Especially preferred "soft" monomers include the alkyl acrylate and methacrylate esters and the alkyl vinyl ethers. The "hard" and "soft" monomer charges are manipulated so that an interpolymer with a glass transition temperature less than −25° C. is obtained.

The Class B water-soluble carboxylate-containing interpolymers are especially preferred. The Class A polymers exhibit low impedance values, but they also exhibit a tendency to pick up adventitious moisture when in contact with the skin. For most applications not requiring prolonged skin contact such as diagnostic electrocardiography, grounding media for electrosurgery, biofeedback, and the like, Class A materials function satisfactorily. However, for applications requiring relatively long term skin contact such as monitoring electrocardiography, electro-pain stimulation, and the like, Class A materials are less preferred due to their hygroscopic properties. Class C interpolymers, on the other hand, generally offer the best and most stable adhesive performance but generally do not provide high conductivity. The Class B interpolymers represent a very desirable combination of the excellent electrical properties of the Class A polymers and the excellent adhesive properties of the Class C interpolymers.

Examples of preferred electrically conductive polymers for use in the electrode of the invention are listed in the following Table I:

TABLE I

Preferred Class A Polymers

Poly(acrylic acid)neutralized with sodium hydroxide.
Poly(acrylic acid)neutralized with triethanolamine.
Poly(acrylic acid)neutralized with ammonia.
Poly(methacrylic acid)neutralized with triethylamine.

Preferred Class B Interpolymers*

Copoly(iso-octyl acrylate:acrylic acid) (60:40) neutralized with methyldiethanolamine.
Copoly(butyl acrylate:methacrylic acid) (50:50) neutralized with tetramethylammonium hydroxide.
Copoly(2-ethylhexyl methacrylate:acrylic acid) (60:40) neutralized with triethylamine.
Copoly(methyl vinyl ether:maleic acid) (50:50) neutralized with sodium carbonate.
Copoly(2-ethylhexyl vinyl ether:maleic acid) (50:50) neutralized with methyldiethanolamine.

*All ratios are given as molar ratios.

Preferred Class C Interpolymers

Copoly(iso-octyl acrylate:acrylic acid) (90:10) neutralized with triethylamine.
Copoly(butyl acrylate:methacrylic acid) (85:15) neutralized with methyldiethanolamine.
Copoly(butyl acrylate:acrylic acid) (85:15) neutralized with tetramethylammonium hydroxide.

It is obvious that one skilled in the art could vary the extent of neutralization of the carboxyl groups so as to maximize the adhesive properties of the polymer.

When the previously described polymers alone are not sufficiently conformable under use conditions, they can generally be brought within the prescribed limits by plasticization. Plasticization of the polymer or interpolymer can be generally accomplished by adding a more "fluid" ingredient to the polymer. Generally, it is desirable that this external plasticizing agent be compatible with the polymer. The external plasticizer can be any material that will result in transforming a brittle polymer or interpolymer into a conformable having the above-described Williams Plasticity values and/or glass transition temperature. Suitable plasticizers include poly(hydroxyalkanes) such as glycerol, poly(oxyalkylene) alcohols such as poly(oxypropylene) glycol, and the like. Another desirable means of plasticizing the polymers and interpolymers of the present invention is to neutralize the carboxyl group with an alkanolamine having 2 to 12 carbon atoms. These neutralizing agents generally result in more conformable formulations either because of the internal plasticizing effect of the hydroxyl groups or because of their expected ability to retain more water in the formulations compared to conventional amine or Group I metal bases. The preferred alkanolamines are ethanolamine, methyldiethanolamine, diethanolamine and triethanolamine.

It is also contemplated within the scope of the invention to tackify the formulations herein described where necessary, especially to prepare a pressure sensitive adhesive formulation which is a preferred embodiment of the invention. Preferred tackifiers are the water-soluble neutralization products of naturally occurring, normally water-insoluble acid rosins (typically having an acid number in the range of 135–170, although rosins having acid numbers outside this range may also be used) and secondary or tertiary alkanolamines. Especially preferred tackifiers are the water-soluble neutralization products of hydrogenated abietic acid and secondary or tertiary alkanolamines.

DESCRIPTION OF THE DRAWINGS

Further understanding of the invention will be facilitated by reference to the accompanying drawings wherein:

FIG. 1 is a top perspective view of a typical disposable biomedical electrode according to the invention; and FIG. 2 is an enlarged cross-sectional view of the electrode taken along line 2—2 of FIG. 1.

In FIGS. 1 and 2, electrode 10 comprises an electrode plate 12 constructed from an electrically conductive material such as stainless steel, silver, nickel or the like, compressed carbon or graphite, or a metal coated plastic, fabric, or conductive plastic material. The electrode plate has means associated therewith for electrical connection to a lead wire which is, in turn, connected to an electromedical device. In electrode 10, the means for electrical connection to a lead wire are illustrated by connector stud 14, a vertical extension of electrode plate 12. Connector stud 14 is adapted to fit a female receptor of a connector. The skin-contacting surface of electrode plate 12 is coated with a layer 18 of conductive material as hereinbefore defined. Layer 18 is generally between 25 and 100 microns thick. Overlying the upper surface of the electrode plate and extending outward from the periphery thereof is a patch of adhesive tape 20. Adhesive tape 20 aids in holding the electrode securely to the skin of the patient. In the preferred embodiments of the invention, the conductive material of layer 18 is sufficiently adhesive to assist in holding the electrode to the skin. Because layer 18 is conformable and generally tacky, good electrical connection between the electrode plate and the skin is provided without the need for a large and bulky piece of adhesive tape as is required in many prior art disposable electrodes. Thus, the electrode of the present invention can be made smaller and is easier to handle. The side of layer 18 opposite that secured to the electrode plate is optionally provided with a protective release liner 22. Release liner 22 protects the conductive layer 18 and the adhesive side of patch 20 from contamination prior to use.

It will be apparent to one skilled in the art that the biomedical electrode of the invention may be constructed in various ways. The embodiment illustrated is merely an example of a typical disposable electrode of the recording type. Electrodes used for other purposes, e.g. for stimulation, for grounding in electrosurgery, and for biofeedback have different requirements and must be constructed to meet those requirements. All types of non-invasive electrodes which utilize the conductive material of the invention at the interface of the electrode and the skin are contemplated within the scope of the invention.

The invention is further illustrated by the following non-limiting examples.

EXAMPLE 1

Preparation of Poly(Sodium Acrylate) (100 Parts) and Glycerol (43 Parts)

Poly(acrylic acid) having a weight-average molecular weight of about 120,000 (9.7 grams polymer dissolved in 47.3 grams of water), sodium hydroxide (5.3 grams dissolved in 20 grams of water), and glycerol (9.7 grams) were mixed thoroughly.

Electrodes were made by coating the plasticized polymer onto nickel plated discs having an area of approximately 127 mm$^2$ and air drying overnight. A polymer layer having a thickness of 75±25 microns was obtained. The impedance value of the electrodes was obtained by applying an electrode to the skin of the inner forearm of a human male subject. The skin site was prepared by lightly abrading with a #220 open coatealuminum oxide sandpaper, and the abraded area was wiped with a 2 in. (5 cm)×2 in. (5 cm) 12 ply gauze sponge dampened with normal saline solution. The electrode was attached to the skin site while it was still visibly wet with a piece (2.5 cm by 4 cm) of 3M Brand Micropore Tape.

Impedance measurements were made using the method reported by Spach et al., *Circulation* 34, 649–656 (1966). All impedance measurements were made at a frequency of 10 Hertz. The electrode was found to have an impedance value of 30 Kohms.

EXAMPLE 2

Preparation of Copoly(iso-octyl acrylate:Acrylic Acid)(61:39).Triethylamine Salt Iso-octyl acrylate (210 grams), acrylic acid (52.5 grams), and azobis(iso-butyronitrile) (0.656 grams; 0.25 weight percent based on monomer charge) were dissolved in acetone (447.8 grams) achieving a monomer solids of 36.96% by weight. The solution was sparged with nitrogen, sealed, and agitated at 53° C. for 24 hours. The copolymer percent solids as measured by a standard gravimetric procedure was 35.47% by weight (96% reaction), and the inherent viscosity as measured on a 0.1% solution in tetrahydrofuran at 30° C. was 1.88. To 10.5 grams of this solution (3.72 grams of copolymer having a bound acrylic acid content of 0.74 gram (0.0103 mole)) were added 5.07 milliliters (containing 1.04 grams (0.0103 mole) of triethylamine)) of an ethanolic solution of triethylamine (20.6 grams in 100 milliliters of solution) and mixed thoroughly on a mechanical shaker. The interpolymer was incorporated into an electrode as described in Example 1, and the impedance of the bioelectrode was 42 Kohms.

EXAMPLES 3–5

Using the method of Example 2, other conductive materials were prepared and incorporated into electrodes. These electrodes are summarized in the following table:

TABLE I

| Example | Formulation* | Impedance (Kohms) |
|---|---|---|
| 3 | Iso-octyl acrylate: Acrylic Acid (84:16)** + Triethylamine | 100 |
| 4 | Iso-octyl acrylate: Acrylic Acid (78:22)** + Triethylamine | 64 |
| 5 | Iso-octyl acrylate: Acrylic Acid + Triethylamine | 21 (48:52) |

*Triethylamine was added equimolar with respect to the amount of acrylic acid present in the copolymer.
**This carboxylated interpolymer is not water-soluble.

EXAMPLE 6

Preparation of Copoly(n-butyl acrylate:Acrylic acid)(63:37).Methyldiethanolamine Salt n-Butyl acrylate (160 grams), acrylic acid (53.3 grams), acetone (476 grams), and azobis(iso-butyronitrile)(0.5333 gram) were placed in a one liter bottle, sparged briefly with nitrogen, sealed tightly, and heated with agitation at 53° C. for 24 hours. The percent copolymer solids by weight was 28.4%, and the inherent viscosity as described in Example 2 was 2.20. To 57.5 grams of the copolymer solution (containing 16.3 grams of copolymer and 4.1 grams (0.0567 mole) of incorporated acrylic acid)) was added the following solution:

| | |
|---|---|
| Methyldiethanolamine | 8.9 grams |
| Floral AX | 6.5 grams |
| Pycal 94 | 3.3 grams |
| Ethanol | 18.8 grams |

Foral AX (Hercules, Inc.) is a tackifying agent that is essentially hydrogenated abietic acid. Pycal 94 (ICI Americas, Inc.) is a plasticizer that is a phenol-terminated polyoxyalkylene resin. The methyldiethanolamine added was sufficient to neutralize 98 mole percent of all carboxylic acids (both incorporated acrylic acid and Foral AX) present in the formulation. Ethanol was added to maintain solution with the polymeric carboxylate that was forming. The mixture was rotated slowly on a ball mill overnight. The resulting water-soluble interpolymer solution was clear and slightly yellow in color. The formulation when coated and evaluated as in Example 1 had an impedance of 24 Kohms.

EXAMPLE 7

Preparation of Copoly(methyl vinyl ether:maleic acid)(50:50).Potassium Salt

Copoly(methyl vinyl ether:maleic anhydride)(50:50) (Grantrez AN-119 available from GAF)(20.6 grams) was suspended in 80 grams of water and heated on a steam bath to form a 20% solids clear solution of copoly(methyl vinyl ether:maleic acid) (50:50) in water. To 61.8 grams of the solution (containing 12.4 grams of copolymer and 8.26 grams (0.072 mole) of maleic acid)) was added 4.0 grams (0.072 mole) of potassium hydroxide in order to half-neutralize all maleic acid present. Glycerol (9.3 grams) was also added as a plasticizer. The impedance of a bioelectrode prepared with the material was 33 Kohms.

In similar fashion as in Example 7, the sodium salts (using sodium carbonate as neutralizing base) and tetramethyl ammonium salts (using tetramethylammonium hydroxide) were prepared and evaluated. The results are given in the following table:

TABLE II

| Example | Formulation* | Impedance (Kohms) |
|---|---|---|
| 8 | Copoly(methyl vinyl ether:maleic acid) (50:50) + sodium carbonate | 6 |
| 9 | Copoly(methyl vinyl ether:maleic acid)(50:50) + tetramethylammonium hydroxide | 28 |

*The level of neutralization of carboxyl groups was 50 mole percent.

What is claimed is:

1. In an essentially dry disposable biomedical electrode comprising an electrode plate having an upper surface and a lower body-contacting surface, said upper surface having means for electrically connecting said electrode plate to a lead wire, and a conductive material on said body-contacting surface of said electrode plate for enhancing electrical connection with the skin, the improvement wherein said conductive material comprises a dermally-nonirritating, conformable, cohesive, synthetic hydrophilic polymer containing at least 5 mole percent of monomer units containing a salt of a carboxylic acid, said electrode having an impedance of 500 Kohms or less at a frequency of 10 Hertz.

2. The electrode according to claim 1 wherein said polymer is water-soluble.

3. The electrode according to claim 2 wherein said polymer contains at least about 25 mole percent monomer units containing a salt of a carboxylic acid.

4. The electrode according to claim 1 wherein said salt is selected from the group consisting of Group I metal, amine, and quaternary ammonium salts of a carboxylic acid.

5. The electrode according to claim 4 wherein said salt is an amine salt.

6. The electrode according to claim 5 wherein said amine salt is an alkanolamine salt having 2 to 12 carbon atoms inclusive.

7. The electrode according to claim 6 wherein said alkanolamine is selected from the group consisting of ethanolamine, methyldiethanolamine, diethanolamine and triethanolamine.

8. The electrode according to claim 1 wherein said carboxylic acid is selected from the group consisting of acrylic acid, methacrylic acid, and maleic acid.

9. The electrode according to claim 1 wherein said polymer is a copolymer further comprising monomer units free of carboxylic acid groups and carboxylic acid salts and containing alkyl groups having about 4 to 12 carbon atoms.

10. The electrode according to claim 9 wherein said monomer units are selected from the group consisting of alkyl acrylates, alkyl methacrylates, and alkyl vinyl ethers.

11. The electrode according to claim 10 wherein said monomer units are selected from the group consisting of iso-octyl acrylate, butyl acrylate, 2-ethylhexyl methacrylate, methyl vinyl ether, and 2-ethylhexyl vinyl ether.

12. The electrode according to claim 11 wherein said carboxylic acid is selected from the group consisting of acrylic acid, methacrylic acid and maleic acid and said salt is an alkanolamine salt having 2 to 12 carbon atoms.

13. The electrode according to claim 1 wherein said polymer is copoly(n-butyl acrylate:acrylic acid).methyldiethanolamine.

* * * * *